United States Patent
Benson et al.

(10) Patent No.: US 8,177,829 B2
(45) Date of Patent: May 15, 2012

(54) AUXILIARY BALLOON CATHETER

(75) Inventors: Brian Benson, Golden Valley, MN (US); Gary J. Pederson, Jr., Albertville, MN (US); Stanley A. Nordin, Monticello, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1638 days.

(21) Appl. No.: 11/508,692

(22) Filed: Aug. 23, 2006

(65) Prior Publication Data

US 2008/0097464 A1    Apr. 24, 2008

(51) Int. Cl.
*A61F 2/06* (2006.01)

(52) U.S. Cl. .............. 623/1.11; 606/192; 604/96.01; 604/101.01; 604/101.02; 604/101.03; 604/101.04

(58) Field of Classification Search ............. 623/1.15, 623/1.2, 1.35; 604/103.07, 96.01, 101.01–101.05
See application file for complete search history.

(56) References Cited

U.S. PATENT DOCUMENTS

| | | | |
|---|---|---|---|
| 4,896,670 A | 1/1990 | Crittenden | 606/194 |
| 4,906,244 A | 3/1990 | Pinchuk et al. | 606/194 |
| 5,556,383 A | 9/1996 | Wang et al. | 604/96 |
| 5,607,444 A | 3/1997 | Lam | 606/194 |
| 5,613,980 A | 3/1997 | Chauhan | 606/194 |
| 5,669,924 A * | 9/1997 | Shaknovich | 623/1.11 |
| 5,720,735 A | 2/1998 | Dorros | 604/284 |
| 5,749,890 A | 5/1998 | Shaknovich | 606/198 |
| 5,792,415 A | 8/1998 | Hijlkema | 264/530 |
| 5,938,582 A | 8/1999 | Ciamacc, Jr. et al. | |
| 5,948,345 A | 9/1999 | Patel et al. | 264/529 |
| 6,017,324 A | 1/2000 | Tu et al. | 604/96 |
| 6,086,556 A | 7/2000 | Hamilton et al. | 604/96 |
| 6,099,497 A * | 8/2000 | Adams et al. | 604/96.01 |
| 6,129,738 A * | 10/2000 | Lashinski et al. | 606/194 |
| 6,142,973 A * | 11/2000 | Carleton et al. | 604/96.01 |
| 6,210,429 B1 | 4/2001 | Vardi et al. | 623/1.11 |
| 6,242,063 B1 | 6/2001 | Ferrera et al. | 428/35.2 |
| 6,258,073 B1 * | 7/2001 | Mauch | 604/284 |
| 6,270,522 B1 | 8/2001 | Simhambhatla et al. | 623/1.11 |
| 6,284,333 B1 | 9/2001 | Wang et al. | 428/35.5 |
| 6,346,089 B1 | 2/2002 | Dibie | 603/1.15 |

(Continued)

FOREIGN PATENT DOCUMENTS

EP     1369097     12/2003

(Continued)

OTHER PUBLICATIONS

U.S. Appl. No. 11/138,202, filed May 26, 2005, Meyer et al.

(Continued)

*Primary Examiner* — Gary Jackson
*Assistant Examiner* — Katrina Stransky
(74) *Attorney, Agent, or Firm* — Vidas, Arrett & Steinkraus, P.A.

(57) ABSTRACT

A balloon catheter may comprise a primary inflation balloon and a secondary inflation balloon located to one side of the primary inflation balloon. The secondary balloon comprises a first portion and a second portion, the first portion located closer to the primary balloon. The second portion has a greater size than the first portion, and a portion of the second portion extends outwardly beyond the first portion and overhangs the first portion. In some embodiments, a cross-sectional shape of the secondary balloon in an inflated state comprises a mushroom shape.

17 Claims, 4 Drawing Sheets

U.S. PATENT DOCUMENTS

| | | | |
|---|---|---|---|
| 6,352,551 B1 | 3/2002 | Wang | 623/1.11 |
| 6,491,710 B2 | 12/2002 | Satake | |
| 6,596,219 B2 | 7/2003 | Dutta et al. | 264/515 |
| 6,709,440 B2* | 3/2004 | Matin et al. | 606/108 |
| 2002/0120320 A1 | 8/2002 | Wang et al. | |
| 2002/0183763 A1* | 12/2002 | Callol et al. | 606/108 |
| 2002/0183780 A1* | 12/2002 | Wang | 606/194 |
| 2003/0093109 A1* | 5/2003 | Mauch | 606/194 |
| 2003/0097169 A1 | 5/2003 | Brucker et al. | 623/1.11 |
| 2003/0163082 A1 | 8/2003 | Mertens | 604/43 |
| 2004/0260330 A1 | 12/2004 | Maeda et al. | 606/194 |
| 2005/0015108 A1* | 1/2005 | Williams et al. | 606/194 |
| 2005/0060027 A1* | 3/2005 | Khenansho et al. | 623/1.35 |
| 2005/0102019 A1* | 5/2005 | Yadin | 623/1.11 |
| 2007/0239111 A1* | 10/2007 | Venturelli | 604/101.01 |

FOREIGN PATENT DOCUMENTS

| | | |
|---|---|---|
| WO | 0112255 | 2/2001 |
| WO | 03074118 | 9/2003 |
| WO | 2006053106 | 5/2006 |

OTHER PUBLICATIONS

U.S. Appl. No. 11/138,196, filed May 26, 2005, Gregorich et al.
U.S. Appl. No. 11/138,022, filed May 26, 2005, Gregorich et al.
U.S. Appl. No. 11/085,780, filed Mar. 21, 2005, Weber et al.
U.S. Appl. No. 10/849,742, filed May 20, 2004, Chen et al.
U.S. Appl. No. 11/265,388, filed Nov. 1, 2005, Noddin.

* cited by examiner

AUXILIARY BALLOON CATHETER

CROSS-REFERENCE TO RELATED APPLICATIONS

Not Applicable

STATEMENT REGARDING FEDERALLY SPONSORED RESEARCH

Not Applicable

BACKGROUND OF THE INVENTION

1. Field of the Invention

In some embodiments this invention relates to implantable medical devices, their manufacture, and methods of use. Some embodiments are directed to delivery systems, such as catheter systems of all types, which are utilized in the delivery of such devices. Some embodiments are directed to the manufacture and preparation of said delivery systems.

2. Description of the Related Art

Within the vasculature, it is not uncommon for stenoses to form at a vessel bifurcation. A bifurcation is an area of the vasculature or other portion of the body where a first (or parent) vessel is bifurcated into two or more branch vessels. Where a stenotic lesion or lesions form at such a bifurcation, the lesion(s) can affect only one of the vessels (i.e., either of the branch vessels or the parent vessel) two of the vessels, or all three vessels. Many prior art stents however are not wholly satisfactory for use where the site of desired application of the stent is juxtaposed or extends across a bifurcation in an artery or vein such, for example, as the bifurcation in the mammalian aortic artery into the common iliac arteries.

Stents intended for deployment at a vessel bifurcation often require specialized delivery systems that include more parts than a traditional delivery catheter. While auxiliary portions of a delivery system have been successful in expanding portions of stents into a side branch vessel, there remains a need for devices that are particularly suitable for expanding stents at a bifurcation to achieve an ideal expanded configuration.

The art referred to and/or described above is not intended to constitute an admission that any patent, publication or other information referred to herein is "prior art" with respect to this invention. In addition, this section should not be construed to mean that a search has been made or that no other pertinent information as defined in 37 C.F.R.§1.56(a) exists.

All US patents and applications and all other published documents mentioned anywhere in this application are incorporated herein by reference in their entirety.

Without limiting the scope of the invention a brief summary of some of the claimed embodiments of the invention is set forth below. Additional details of the summarized embodiments of the invention and/or additional embodiments of the invention may be found in the Detailed Description of the Invention below.

A brief abstract of the technical disclosure in the specification is provided as well only for the purposes of complying with 37 C.F.R. 1.72. The abstract is not intended to be used for interpreting the scope of the claims.

BRIEF SUMMARY OF THE INVENTION

In at least one embodiment, the invention is directed to a balloon catheter comprising a catheter shaft having an internal catheter lumen, a primary balloon, a side branch shaft having an internal branch lumen and a secondary balloon. The secondary balloon comprises an inflatable body portion having an internal volume in fluid communication with the branch lumen. The inflatable body portion comprises a first portion and a second portion, the first portion being located closer to the primary balloon than the second portion. The first portion comprises a substantially tubular shape. The second portion has a larger cross-sectional area than the first portion.

In at least one other embodiment, the invention is directed to a balloon catheter comprising a catheter shaft having an internal catheter lumen, a primary balloon, a side branch shaft having an internal branch lumen and a secondary balloon. The secondary balloon comprises an inflatable body portion having an internal volume in fluid communication with the branch lumen. The inflatable body portion comprises a first portion and a second portion, the first portion being located closer to the primary balloon than the second portion. A first maximum distance measured across the first portion is less than a second maximum distance measured across the second portion. The first maximum distance is measured at a location in the lower half of the height of the secondary balloon and the second maximum distance is measured at a location in the upper half of the height of the secondary balloon.

In at least one other embodiment, the invention is directed to a balloon catheter comprising a catheter shaft having an internal catheter lumen, a primary balloon, a side branch shaft having an internal branch lumen and a secondary balloon. The secondary balloon comprises an inflatable body portion having an internal volume in fluid communication with the branch lumen. The inflatable body portion comprises a first portion and a second portion, the first portion being located closer to the primary balloon than the second portion. The second portion has a larger cross-sectional area than the first portion, and the secondary balloon comprises a non-spherical shape.

In at least one other embodiment, the invention is directed to a method comprising providing a balloon catheter having a primary balloon, a secondary balloon and a stent. The secondary balloon is located beside the primary balloon. The secondary balloon comprises a first portion and a second portion, the second portion in an inflated state having a larger cross-sectional area than the first portion. The first portion is located closer to the primary balloon than the second portion. The stent comprises an outwardly expandable side branch petal structure. The stent is oriented about the balloon catheter with the secondary balloon positioned beneath the petal structure. The method further comprises delivering the stent to a deployment site at a vessel bifurcation having a side branch vessel, inflating the primary balloon to expand the stent, and inflating the secondary balloon to unfold the petal structure into the side branch vessel.

These and other embodiments which characterize the invention are pointed out with particularity in the claims annexed hereto and forming a part hereof. However, for further understanding of the invention, its advantages and objectives obtained by its use, reference can be made to the drawings which form a further part hereof and the accompanying descriptive matter, in which there is illustrated and described a embodiments of the invention.

BRIEF DESCRIPTION OF THE SEVERAL VIEWS OF THE DRAWING(S)

A detailed description of the invention is hereafter described with specific reference being made to the drawings.

DETAILED DESCRIPTION OF THE INVENTION

Figure 1:
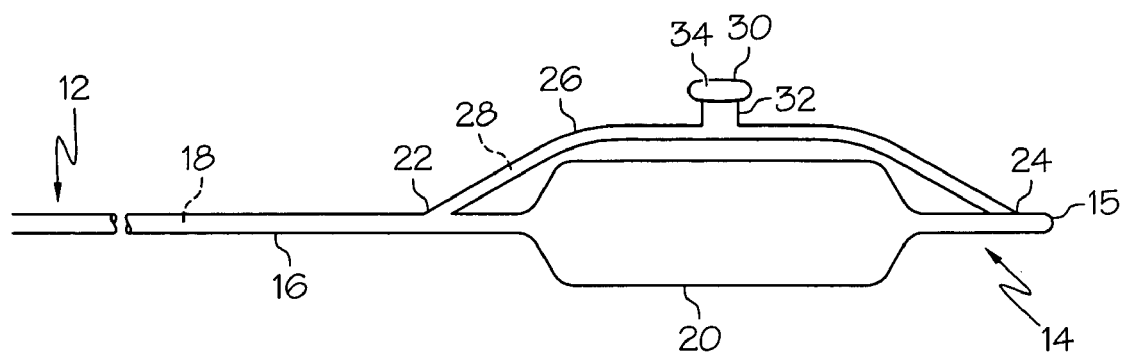
FIG. 1 shows an embodiment of a catheter having a shaped secondary balloon.

While this invention may be embodied in many different forms, there are described in detail herein specific embodiments of the invention. This description is an exemplification of the principles of the invention and is not intended to limit the invention to the particular embodiments illustrated.

For the purposes of this disclosure, like reference numerals in the figures shall refer to like features unless otherwise indicated.

FIG. 1 shows an embodiment of a balloon catheter 10 having a shaped secondary balloon 30. The catheter 10 comprises an elongate shaft 16 having an internal lumen 18 extending therethrough. The shaft 16 has a proximal portion 12 and a distal portion 14 that includes a tip 15. In some embodiments, a tip 15 may be softer and/or more flexible than other portions of the shaft 16.

A primary inflation balloon 20 is located in proximity to the distal portion 14 of the shaft 16. An internal volume of the primary balloon 20 is in fluid communication with the internal lumen 18 of the shaft 16, thus allowing the primary balloon 20 to be inflated and deflated.

The secondary balloon 30 is attached to a secondary shaft 26 having an internal lumen 28. An internal volume of the secondary balloon 30 is in fluid communication with the internal lumen 28. A proximal end of the secondary shaft 26 connects to the catheter shaft 16 at a proximal connection location 22, and a distal end of the secondary shaft 26 connects to the catheter shaft 16 at a distal connection location 24. The proximal connection location 22 is located proximal to the primary balloon 20, and the distal connection location 24 is located distal to the primary balloon 20.

In some embodiments, the internal lumen 28 of the secondary shaft 26 is in fluid communication with the internal lumen 18 of the catheter shaft 16. Thus, in some embodiments, the secondary balloon 30 is arranged to inflate and/or deflate simultaneously with the primary balloon 20. In some embodiments, the connection between the two lumens 18, 28 is made at the proximal connection location 22, while the secondary shaft 26 is sealed at the distal connection location 24 or anywhere along the length of the secondary shaft 26 distal to the secondary balloon 30.

In some other embodiments, the secondary balloon 30 is arranged to be inflatable and deflatable independently from the primary balloon 20. In such embodiments, the catheter shaft 16 is provided with a second internal lumen that is in fluid communication with the secondary shaft lumen 28. A second internal lumen of the catheter shaft 16 can extend from the proximal connection location 22 to the proximal end 12 of the shaft 16. Some examples of multiple lumen catheters are discussed in published U.S. Patent Publication No. US2003/0163082, the entire disclosure of which is incorporated herein by reference in its entirety.

The secondary balloon 30 includes a first portion 32 and a second portion 34. In some embodiments, the second portion 34 is stacked above the first portion 32 such that the second portion 34 is located farther away from the catheter shaft 16 and the primary balloon 20 than the first portion 32, for example as measured in a direction radial to the catheter shaft 16. The second portion 34 is generally larger than the first portion 32 across at least one dimension, and in some embodiments, across at least two dimensions. In some embodiments, an internal volume of the second portion 34 is greater than an internal volume of the first portion 32. In some embodiments, the secondary balloon 30 comprises a three-dimensional "mushroom" shape.

Figure 2:
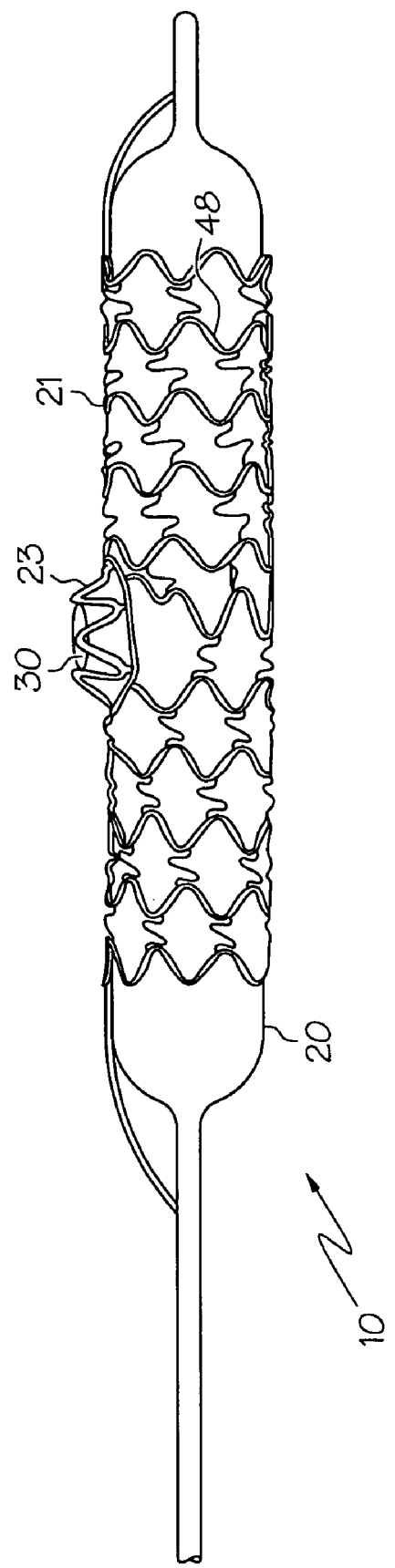
FIG. 2 shows an embodiment of a catheter expanding a stent.

FIG. 2 shows an embodiment of a balloon catheter 10 expanding a stent 48. The stent 48 comprises a main cylindrical framework portion 21 and a plurality of outwardly deployable side branch petal structures 23. The main cylindrical framework portion 21 is expanded in diameter as the primary balloon 20 is inflated. The side branch petals 23 are further outwardly deployed as the secondary balloon 30 is inflated.

Figure 3:
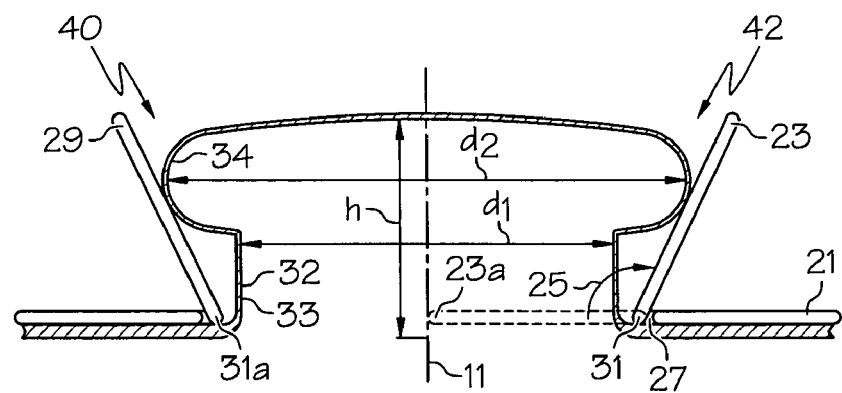
FIG. 3 shows a cross-sectional view of an embodiment of a secondary balloon, as well as stent elements being unfolded by the secondary balloon.

FIG. 3 shows a cross-sectional view of an embodiment of a secondary balloon 30. A first side 40 and a second side 42 of the balloon 30 are symmetrical across a secondary balloon central axis 11. In some embodiments, for example when the secondary balloon 30 comprises a circular cross-sectional shape, the first side 40 and the second side 42 comprise diametrically opposed regions. A diameter of the second portion 34 taken about the central axis 11 is larger than a diameter of the first portion 32. A distance across the second portion 34 as measured between opposing first 40 and second 42 sides is greater than a similar distance across the first portion 32.

The second portion 34 includes an outwardly extending portion 44 that extends outwardly in a radial direction with respect to the central axis 11. The outwardly extending portion 44 forms an outward inclination that overhangs the first portion 32.

In some embodiments, the first portion 32 includes sidewall portions 33 that extend substantially parallel to the central axis 11. In some embodiments, the first portion 32 is substantially tubular in shape. In some embodiments, the first portion 32 is substantially cylindrical in shape.

In some embodiments, a first maximum distance $d_1$ measured across the first portion 32 is less than a second maximum distance $d_2$ measured across the second portion 34. The first maximum distance $d_1$ and the second maximum distance $d_2$ can be measured parallel to one another. The first maximum distance $d_1$ and the second maximum distance $d_2$ can also be measured orthogonal to the central axis 11.

The secondary balloon 30 defines a height h that can be measured in the radial direction of the catheter shaft 16. In some embodiments, the height h can be measured from a central axis of the secondary shaft 26 to the top of the secondary balloon 30. In some embodiments, the height h can be measured from the bottom of the first portion 32 to the top of the second portion 34. In some embodiments, the first portion 32 can define approximately a lower half of the height h and the second portion 34 can define approximately an upper half of the height h.

In some embodiments, the first maximum distance $d_1$ is located in a lower half of the height h, and the second maximum distance $d_2$ is located in an upper half of the height h. In some other embodiments, the second maximum distance $d_2$ can be located in an upper ¼ of the height h or even an upper ⅛ of the height h. The second maximum distance $d_2$ is generally located farther away from the primary balloon 20 than the first maximum distance $d_1$.

The secondary balloon 30 can be used to extend or unfold portions of a stent into a side branch vessel at a bifurcation. Some stents include a dedicated side branch structure, wherein a plurality of "petals" may be outwardly deployed by a secondary balloon 30. Some examples of stents with side branch petal structures are disclosed in U.S. Patent Publication Nos. US 2003/0163082, US 2005/0060027, US 2006/0271161, US 2006/0271160 and US 2006/0271159, the entire disclosures of which are hereby incorporated herein by reference in their entireties.

FIG. 3 shows portions of a stent including a main cylindrical framework portion 21 and an outwardly expandable side branch petal portion 23. Each petal 23 is connected to the main framework 21 at a connection 27. Prior to outward deployment of the petals 23, each unexpanded petal 23a may be aligned with the framework portion 21 and may be oriented substantially parallel to the catheter shaft 16. The secondary balloon 30 would be in a deflated and folded state beneath the unexpanded petal 23a.

During inflation of the secondary balloon 30 and the resulting unfolding deployment of the petals 23, each petal 23 generally pivots about at least one pivot point 31, or in some embodiments, a rotation axis. In some embodiments, the pivot point 31 comprises a connection 27 as the connection 27 yields.

A rotation angle 25 comprises an angle measured about the pivot point/axis 31 between the unexpanded petal 23a configuration and the deployed petal 23 configuration. The shape of the secondary balloon 30 allows the rotation angle to be greater than 90 degrees. Various embodiments of a secondary balloon 30 are configured to provide any suitable rotation angle 26, for example ranging from 90 degrees to 150 degrees or more. In some embodiments, a secondary balloon 30 may be shaped to provide rotation angles of 100 degrees, 110 degrees, 120 degrees, 130 degrees, 140 degrees, etc.

A stent may include a first petal 23 and a second petal 29 that are located opposite one another across the side branch structure. A distance may be measured between the rotation point/axis 31 of the first petal 23 and the rotation point/axis 31a of the second petal 29. In some embodiments of a secondary balloon 30, a distance across the first portion 32 between opposing first 40 and second 42 sides is less than the distance between the rotation points 31, 31a of opposing petals 23, 29. A distance across the second portion 34 as measured between opposing first 40 and second 42 sides is greater than the distance between the rotation points 31, 31a of opposing petals 23, 29.

A secondary balloon 30 may be made using any suitable method. In some embodiments, a balloon 30 is injection molded. In some embodiments, a balloon 30 is blow molded from a preform. In some embodiments, the preform comprises a tube that forms both the secondary shaft 26 and the secondary balloon 30. In some embodiments, a balloon 30 is formed using a layer-by-layer deposit process that uses electrostatic interaction between oppositely charged particle layers, for example as described in U.S. patent application Ser. Nos. 11/085,780, 10/849,742 and 11/085,780, the entire disclosures of which are hereby incorporated herein by reference in their entireties.

In some embodiments, further operations are performed on a secondary balloon 30 to achieve desired wall configurations. For example, material may be removed from certain portions of the balloon 30 wall to achieve desired strength or flexibility characteristics. In some embodiments, score lines may be formed in the balloon 30 wall to encourage predetermined folding patterns. Such operations include drilling, notching, punching, abrasive machining, water-jet machining, computer-numeric-control (CNC) machining, laser ablation, chemically dissolution, etc The balloons according to the invention may be formed from any suitable balloon material which can be molded as described. Suitable classes of materials include, but are not limited to, polyolefins, polyamides (e.g. nylons or aramids), polyesters and copolyesters, polyurethanes, polyethers, polyimides, polycarbonates, etc. Copolymers are suitable for use as well.

Examples of suitable polyesters include, but are not limited to, polyethylene terephthalate (PET), polybutylene terephthalate (PBT), polyethylene naphthalate (PEN), etc.

HYTREL®, polyester-ester elastomers available from DuPont Wilmington, Del. and ARNITEL® polyester-esters and polyether-esters available from DSM Engineering Plastics—Americas in Evansville, Ind. may also be employed herein. These polymers are available in different grades depending on desired balloon properties.

PEBA block copolymers, such as poly(ether-block-amide) block copolymers available under the tradename of PEBAX® from Arkema in Paris, France, may be employed herein. PEBAX® is available in different grades, for example, 6333, 7033 and 7233 are all suitable depending on the balloon properties desired. Suitable polyamides include, but are not limited to, nylon 6, nylon 10, nylon 11 and nylon 12.

Polyurethanes are available commercially under the tradenames of ISOPLAST® and PELLETHANE® from Dow Chemical Co. in Midland, Mich.

These and other suitable balloon materials are described in U.S. Pat. Nos. 4,906,244, 5,556,383, 5,792,415, 5,948,345, 6,086,556 and 6,270,522, the entire contents of which are incorporated by reference herein. The present invention is not limited by the polymeric material which may be employed herein.

Reinforcement materials such as liquid crystal polymers may also be employed herein. Liquid crystal polymers are described for use in balloons in U.S. Pat. Nos. 6,242,063, 6,284,333 and 6,596,219, the entire contents of which are incorporated by reference herein.

The above lists are intended for illustrative purposes only, and not intended to limit the scope of the present invention. Selection of balloon materials is known to those of skill in the art.

In some embodiments, the second portion 34 is made from a different material than the first portion 32.

In some embodiments, the second portion 34 of a secondary balloon 30 will assume a first inflated shape at a first pressure and a second inflated shape at a second, higher pressure, while the first portion assumes substantially the same shape at both the first and second pressures. In some embodiments, the compliance of the second portion 34 is different from the compliance of the first portion 32, and thus the secondary balloon 30 comprises a stepped compliance balloon.

Figure 4:
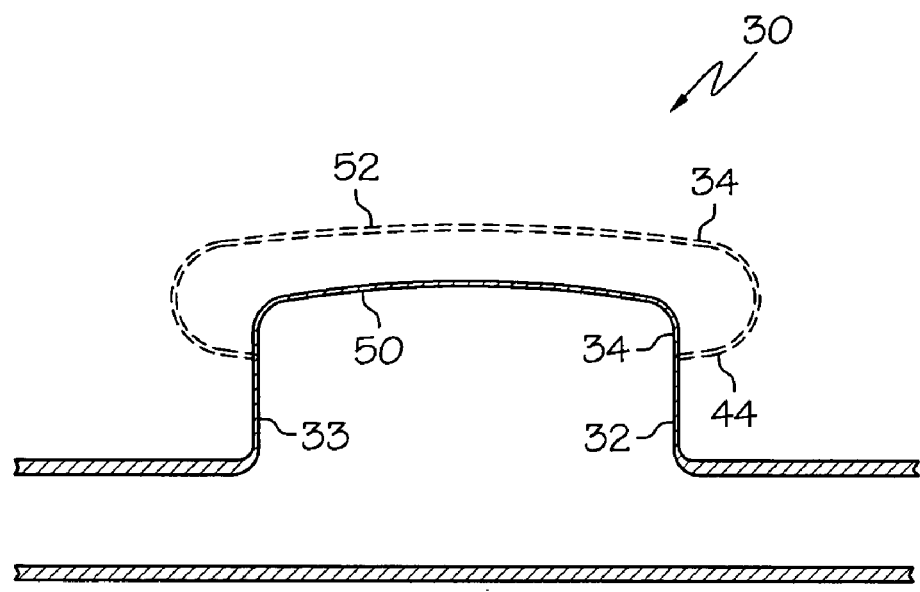
FIG. 4 shows an embodiment of a secondary balloon that assumes one inflated configuration at a first inflation pressure and a second inflated configuration at a second inflation pressure.

FIG. 4 shows a sectional view of an embodiment of a secondary balloon 30 capable of assuming different shapes at different pressures. When the balloon 30 is inflated to a first pressure, the second portion 34 assumes a first inflated configuration 50, wherein the sidewall 33 of the second portion 34 is generally parallel to the sidewall 33 of the second portion 32. The second portion 34 generally comprises an extension of the first portion 32, and a diameter of the second portion 34 is substantially equal to the diameter of the first portion 32.

As the balloon 30 is inflated to a higher pressure, the shape of the first portion 32 remains substantially the same, while the shape of the second portion 34 changes. The second portion 34 assumes a second inflated configuration 52, wherein the second portion 34 includes an outwardly extending portion 44 that overhangs the first portion 32.

Such balloons 30 that are capable of assuming different shapes at different pressures may be manufactured according to any suitable method. In some embodiments, the balloon 30 may be molded to the second inflated configuration 52 under heat and high pressure, allowed to shrink by reducing the internal pressure, and then molded to the first inflated configuration 50 at a moderate pressure. Some embodiments may further be manufactured according to the methods disclosed in U.S. Pat. No. 6,352,551 to Wang, the entire disclosure of which is hereby incorporated herein by reference in its entirety. Some other embodiments may be made by selectively treating either the first portion 32 or the second portion 34, for example to selectively strengthen or weaken either portion 32, 34 as desired. In some embodiments, operations are performed on the first portion 32 to cause cross-linking, resulting in a first portion 32 that is more resistant to yielding and strain elongation. In some embodiments, the first portion 32 is reinforced, for example by placing an overcoating such as a tube about the first portion 32. A portion of a balloon 30 may further be reinforced according to methods disclosed in U.S. patent application Ser. No. 11/265,388 to Noddin, the entire disclosure of which is hereby incorporated herein by reference in its entirety.

In some embodiments, the primary balloon 20 and the secondary balloon 30 have cooperatively arranged compliance curves, wherein the balloons 20, 30 assume various predetermined shapes at various predetermined pressures. For example, in some embodiments, the primary balloon 20 reaches its full expanded configuration at a first pressure and the secondary balloon 30 reaches its full expanded configuration at a second, higher pressure. In some embodiments, the primary balloon 20 reaches its full expanded configuration at a first pressure and the secondary balloon 30 reaches a first expanded shape 50 at a second, higher pressure. Upon further inflation, the secondary balloon 30 will expand to a second expanded shape 52 at a third, even higher pressure.

Figure 5:
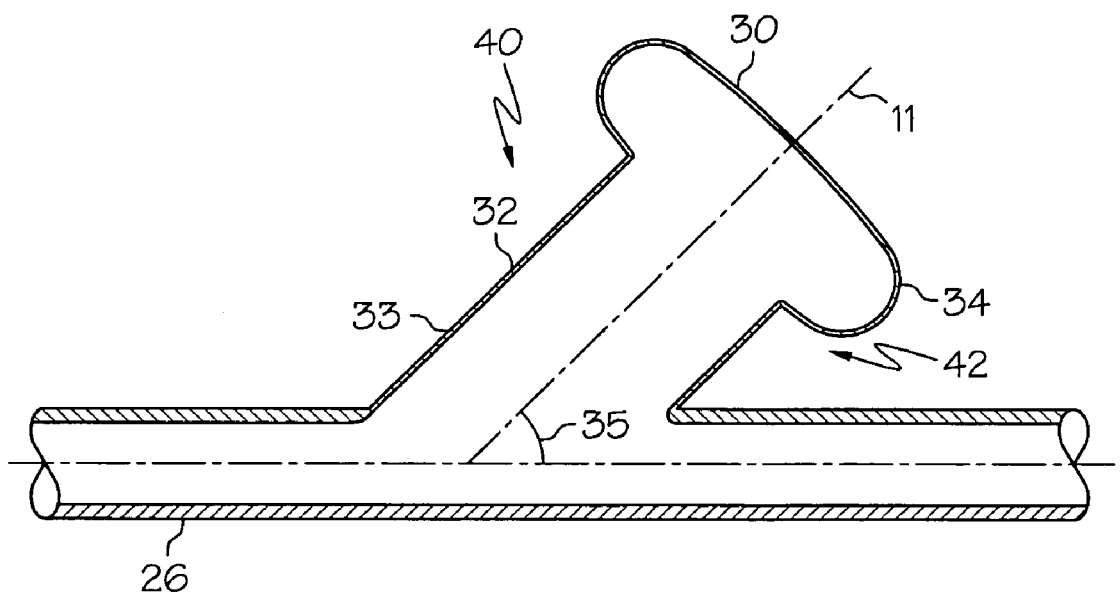
FIG. 5 shows a cross-sectional view of another embodiment of a secondary balloon.

FIG. 5 shows a sectional view of another embodiment of a secondary balloon 30, wherein the central axis 11 is oriented at a non-perpendicular angle 35 to the secondary shaft 26. Various non-perpendicular embodiments have an angle 35 of any suitable amount, for example ranging from less than 20 degrees to just under 90 degrees. The length of a sidewall 33 of the first portion 32 is longer on a first side 40 than the length of an opposed sidewall of the first portion 32 on the second side 42. It should be noted that various non-perpendicular embodiments can be oriented in any suitable direction, for example being slanted toward the distal end of the catheter, being slanted away from the distal end of the catheter, or being slanted in a non-axial direction of the catheter, such as being slanted in a direction that is circumferential with respect to the catheter.

The non-perpendicular angle 35 is well suited for vessel bifurcations where an angle between a main branch vessel and a side branch vessel is less than 90 degrees. Desirably, the angle 35 may be selected to match an angle between the main branch vessel and the side branch vessel.

The non-perpendicular angle 35 is also suitable for high stent petal 23 rotation angles 25 (see FIG. 3). Some embodiments are suitable for deploying petals 23 at rotation angles 25 of 170 degrees or more.

Figure 6:
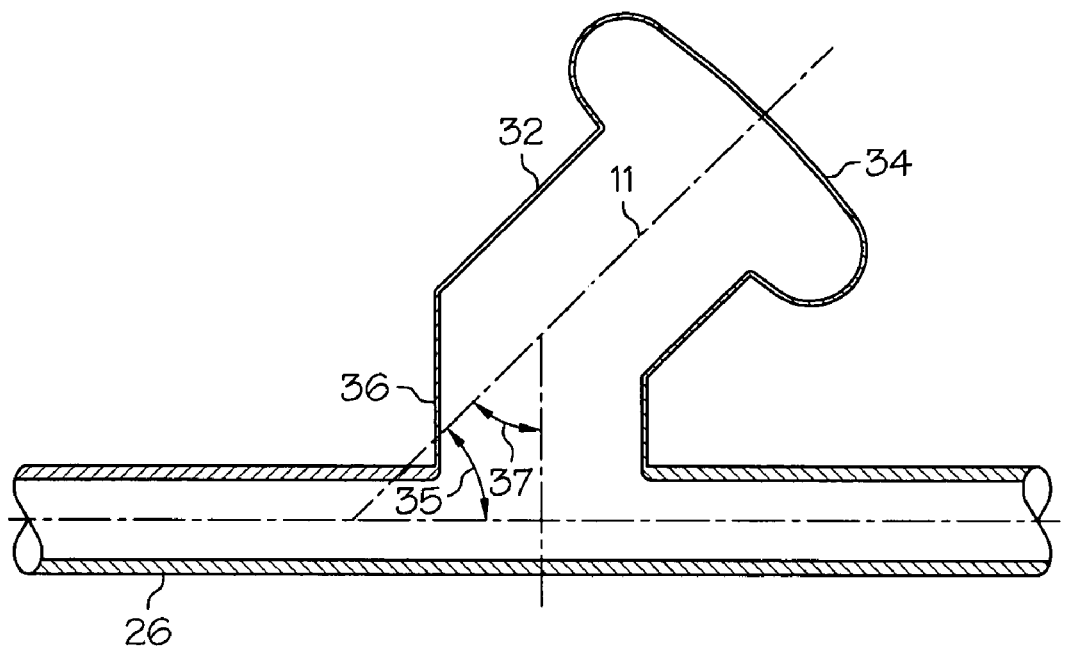
FIG. 6 shows a cross-sectional view of another embodiment of a secondary balloon.

FIG. 6 shows a sectional view of another embodiment of a secondary balloon 30, wherein the central axis 11 of the first portion 32 and the second portion 34 is oriented at a non-perpendicular angle 35 to the secondary shaft 26. The balloon 30 comprises a base portion 36 having a central axis 11 that extends at an angle 37 to the central axis 11 of the first portion 32. The central axis 11 of the base portion 36 extends perpendicular to the secondary shaft 26.

Figure 7:
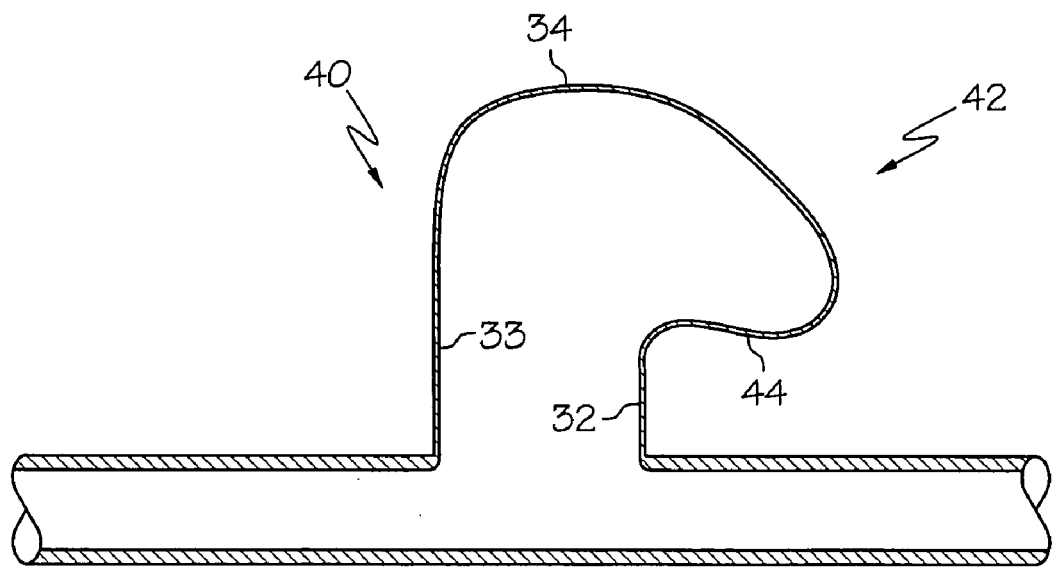
FIG. 7 shows a cross-sectional view of another embodiment of a secondary balloon.

FIG. 7 shows a sectional view of another embodiment of a secondary balloon 30, wherein the second portion 34 comprises an asymmetrical shape. The first side 40 of the second portion 34 comprises an extension of the sidewall 33 of the first portion 32 that extends substantially parallel to the sidewall 33 of the first portion 32. The second side 42 of the second portion 34 comprises an outwardly extending portion 44 that overhangs the first portion 32.

In some embodiments, the first and second portions 32, 34 assume a tubular, substantially symmetrical shape at a first inflation pressure, and the second portion 34 will further expand to the asymmetrical shape having the outwardly extending portion 44 at a second, higher pressure.

The above disclosure is intended to be illustrative and not exhaustive. This description will suggest many variations and alternatives to one of ordinary skill in this art. The various elements shown in the individual figures and described above may be combined or modified for combination as desired. All these alternatives and variations are intended to be included within the scope of the claims where the term "comprising" means "including, but not limited to."

Further, the particular features presented in the dependent claims can be combined with each other in other manners within the scope of the invention such that the invention should be recognized as also specifically directed to other embodiments having any other possible combination of the features of the dependent claims. For instance, for purposes of claim publication, any dependent claim which follows should be taken as alternatively written in a multiple dependent form from all prior claims which possess all antecedents referenced in such dependent claim if such multiple dependent format is an accepted format within the jurisdiction (e.g. each claim depending directly from claim 1 should be alternatively taken as depending from all previous claims). In jurisdictions where multiple dependent claim formats are restricted, the following dependent claims should each be also taken as alternatively written in each singly dependent claim format which creates a dependency from a prior antecedent-possessing claim other than the specific claim listed in such dependent claim below.

This completes the description of the invention. Those skilled in the art may recognize other equivalents to the specific embodiment described herein which equivalents are intended to be encompassed by the claims attached hereto.

The invention claimed is:

1. A balloon catheter comprising:
a catheter shaft having an internal catheter lumen;
a primary balloon;
a side branch shaft having an internal branch lumen;
a stent comprising a side branch assembly comprising a first petal and a second petal; the first petal located across the side branch assembly from the second petal, said first petal arranged to unfold at a first location, said second petal arranged to unfold at a second location, a predetermined distance extending between said first location and said second location; and
a secondary balloon arranged to unfold said first and second petals, the secondary balloon comprising:

an inflatable body portion having an internal volume in fluid communication with the branch lumen, the inflatable body portion comprising a first portion and a second portion, the second portion having a larger cross-sectional area than the first portion, the first portion located closer to the primary balloon than the second portion, a distance across said first portion being less than said predetermined distance, a distance across said second portion being greater than said predetermined distance;

wherein the secondary balloon comprises a substantially cylindrical shape at a first inflation pressure, and the second portion assumes a shape having an outwardly extending portion that overhangs the first portion at a second, higher inflation pressure.

2. The balloon catheter of claim 1, wherein a central axis of the secondary balloon is oriented at a nonperpendicular angle to a central axis of the primary balloon.

3. The balloon catheter of claim 1, wherein the second portion comprises an outwardly extending portion that overhangs the first portion.

4. The balloon catheter of claim 1, wherein a cross-sectional shape of the secondary balloon comprises a mushroom shape.

5. The balloon catheter of claim 1, wherein a cross-section of a sidewall of the second portion comprises a C-shape.

6. A balloon catheter comprising:
a catheter shaft having an internal catheter lumen;
a primary balloon;
a side branch shaft having an internal branch lumen; and
a secondary balloon comprising:
an inflatable body portion having an internal volume in fluid communication with the branch lumen, the inflatable body portion comprising a first portion and a second portion, the first portion comprising a substantially cylindrical shape, the second portion having a larger cross-sectional area than the first portion, the first portion located closer to the primary balloon than the second portion;
wherein the second portion comprises a shape that is asymmetrical across a central axis of the secondary balloon.

7. The balloon catheter of claim 1, wherein the secondary balloon comprises a stepped compliance balloon.

8. The balloon catheter of claim 1, wherein the secondary balloon comprises a non-cylindrical shape at said second, higher inflation pressure.

9. The balloon catheter of claim 1, wherein an internal volume of the second portion is greater than an internal volume of the first portion.

10. A balloon catheter comprising:
a catheter shaft having an internal catheter lumen;
a primary balloon;
a side branch shaft having an internal branch lumen;
a stent comprising a side branch assembly comprising a first petal and a second petal; the first petal located across the side branch assembly from the second petal, said first petal arranged to unfold at a first location, said second petal arranged to unfold at a second location, a predetermined distance extending between said first location and said second location; and
a secondary balloon arranged to unfold said first and second petals, the secondary balloon comprising:
an inflatable bod portion having an internal volume in fluid communication with the branch lumen, the inflatable body portion comprising a first portion and a second portion, the second portion having a larger cross-sectional area than the first portion, the first portion located closer to the primary balloon than the second portion, a distance across said first portion being less than said predetermined distance, a distance across said second portion being greater than said predetermined distance;
the secondary balloon constructed and arranged to unfold each of said side branch petals at least 100 degrees as the secondary balloon is inflated.

11. The balloon catheter of claim 1, wherein the internal catheter lumen is in fluid communication with the internal branch lumen.

12. The balloon catheter of claim 1, said internal catheter lumen comprising a first internal catheter lumen, the catheter shaft further comprising a second internal lumen in fluid communication with the internal branch lumen, said internal branch lumen not in fluid communication with said first internal catheter lumen.

13. The balloon catheter of claim 1, wherein the inflatable body portion defines a height including a lower half and an upper half, the distance across said first portion is measured at a location in the lower half of the height and the distance across said second portion is measured at a location in the upper half of the height.

14. A method comprising:
providing a balloon catheter having a primary balloon, a secondary balloon and a stent, the secondary balloon located beside the primary balloon, the secondary balloon comprising a first portion and a second portion, the first portion comprising a substantially cylindrical shape, the second portion in an inflated state having a larger cross-sectional area than the first portion, the first portion located closer to the primary balloon than the second portion, the stent comprising an outwardly expandable side branch petal structure comprising a first petal and a second petal, the first petal located across the side branch structure from the second petal, said first petal arranged to unfold at a first location, said second petal arranged to unfold at a second location, a predetermined distance extending between said first location and said second location, a distance across said first portion being less than said predetermined distance, a distance across said second portion being greater than said predetermined distance, the stent oriented about the balloon catheter with the secondary balloon positioned beneath the petal structure;
delivering the stent to a deployment site at a vessel bifurcation having a side branch vessel;
inflating the primary balloon to expand the stent; and
inflating the secondary balloon to unfold the petal structure into the side branch vessel, wherein the first and second petals each pivot at least 100 degrees.

15. The method of claim 14, the secondary balloon assuming a first inflated shape at a first inflation pressure and a second inflated shape at a second, higher pressure, a portion of the second portion overhanging the first portion in the second inflated shape.

16. The method of claim 15, wherein the first and second petals each pivot less than 90 degrees as the secondary balloon is inflated to the first inflation pressure.

17. The method of claim 16, wherein the first and second petals each pivot at least 100 degrees from their original configuration as the secondary balloon is inflated to the second inflation pressure.

* * * * *